(12) United States Patent
Dennis

(10) Patent No.: US 8,366,726 B2
(45) Date of Patent: Feb. 5, 2013

(54) VESSEL OCCLUSION CLIP AND APPLICATION THEREOF

(75) Inventor: William G. Dennis, Jacksonville, FL (US)

(73) Assignee: Gyrx LLC, Jacksonville, FL (US)

( * ) Notice: Subject to any disclaimer, the term of this patent is extended or adjusted under 35 U.S.C. 154(b) by 944 days.

(21) Appl. No.: 12/052,802

(22) Filed: Mar. 21, 2008

(65) Prior Publication Data

US 2009/0240266 A1  Sep. 24, 2009

(51) Int. Cl.
*A61B 17/04* (2006.01)
(52) U.S. Cl. .......................... 606/158; 606/157; 606/151
(58) Field of Classification Search .................. 606/120, 606/151, 157, 158, 232; 251/4, 9; 132/137, 132/223, 255; 248/231.51; 16/335, 336; 24/530, 499–509, 334, 521; 383/68
See application file for complete search history.

(56) References Cited

U.S. PATENT DOCUMENTS

| | | | | |
|---|---|---|---|---|
| 1,741,457 A | * | 12/1929 | Glass | 606/210 |
| 2,102,286 A | * | 12/1937 | Schmitt | 132/255 |
| 2,496,109 A | * | 1/1950 | Terry | 24/530 |
| 3,378,010 A | * | 4/1968 | Codling et al. | 606/157 |
| 3,705,586 A | * | 12/1972 | Sarracino | 606/120 |
| 3,867,944 A | * | 2/1975 | Samuels | 606/158 |
| 4,200,088 A | | 4/1980 | Denniston, Jr. | |
| 4,274,415 A | | 6/1981 | Kanamoto et al. | |
| 4,325,377 A | | 4/1982 | Boebel | |
| 4,394,864 A | | 7/1983 | Sandhaus | |
| 4,553,294 A | * | 11/1985 | Larsen | 24/489 |
| 4,556,060 A | | 12/1985 | Perlin | |
| 4,658,822 A | | 4/1987 | Kees, Jr. | |
| 4,877,028 A | | 10/1989 | Sandhaus | |
| 4,961,743 A | * | 10/1990 | Kees et al. | 606/158 |
| 4,966,603 A | | 10/1990 | Focelle et al. | |
| 4,967,949 A | | 11/1990 | Sandhaus | |
| 4,976,722 A | | 12/1990 | Failla | |
| 4,979,950 A | | 12/1990 | Transue et al. | |
| 5,002,552 A | | 3/1991 | Casey | |
| 5,030,226 A | | 7/1991 | Geen et al. | |
| 5,062,846 A | * | 11/1991 | Oh et al. | 606/158 |
| 5,312,426 A | | 5/1994 | Segawa et al. | |
| 5,330,442 A | * | 7/1994 | Green et al. | 606/232 |
| 5,342,373 A | | 8/1994 | Stefanchik et al. | |
| 5,474,567 A | | 12/1995 | Stefanchik et al. | |
| 5,571,121 A | * | 11/1996 | Heifetz | 606/158 |
| 5,575,802 A | | 11/1996 | McQuilkin et al. | |
| 5,593,414 A | | 1/1997 | Shipp et al. | |
| 5,601,573 A | | 2/1997 | Fogelberg et al. | |
| 5,601,574 A | | 2/1997 | Stefanchik et al. | |
| 5,634,932 A | | 6/1997 | Schmidt | |
| 5,681,330 A | | 10/1997 | Hughett et al. | |
| 5,833,700 A | | 11/1998 | Fogelberg et al. | |
| 5,858,018 A | | 1/1999 | Shipp et al. | |
| 5,921,997 A | | 7/1999 | Fogelberg et al. | |
| 5,993,465 A | | 11/1999 | Shipp et al. | |

(Continued)

*Primary Examiner* — Corrine M McDermott
*Assistant Examiner* — Todd J Scherbel
(74) *Attorney, Agent, or Firm* — Hunton & Williams LLP

(57) ABSTRACT

An occlusion clip for permanently occluding a bodily vessel, such as the vas deferens. The occlusion clip has a first leg, a second leg, joined on their proximal ends by a spring coil. The spring coil provides a biased torsional force to the first leg and the second leg, to force them into a closed position. The first leg and the second leg have on their distal ends a vessel occlusion portion that occludes the targeted vessel when the clip is in a closed position.

13 Claims, 8 Drawing Sheets

U.S. PATENT DOCUMENTS

| | | | |
|---|---|---|---|
| 6,179,850 B1 * | 1/2001 | Goradia | 606/158 |
| 6,241,740 B1 | 6/2001 | Davis et al. | |
| 6,273,903 B1 * | 8/2001 | Wilk | 606/219 |
| 6,290,575 B1 | 9/2001 | Shipp | |
| 6,350,269 B1 | 2/2002 | Shipp et al. | |
| 6,516,500 B2 * | 2/2003 | Ogino et al. | 24/504 |
| 6,527,786 B1 | 3/2003 | Davis et al. | |
| 6,537,289 B1 | 3/2003 | Kayan et al. | |
| 6,776,783 B1 * | 8/2004 | Frantzen et al. | 606/151 |
| 6,817,064 B2 * | 11/2004 | Kim et al. | 16/335 |
| 6,842,951 B1 * | 1/2005 | Barre et al. | 24/499 |
| 7,077,851 B2 * | 7/2006 | Lutze et al. | 606/158 |
| 7,322,995 B2 * | 1/2008 | Buckman et al. | 606/157 |
| 7,713,276 B2 * | 5/2010 | Dennis | 606/151 |
| 2002/0013589 A1 | 1/2002 | Callister et al. | |
| 2002/0029051 A1 | 3/2002 | Callister et al. | |
| 2002/0059936 A1 | 5/2002 | Burton et al. | |
| 2003/0176879 A1 * | 9/2003 | Anderson et al. | 606/158 |
| 2005/0021061 A1 | 1/2005 | Dennis | |
| 2005/0021062 A1 | 1/2005 | Dennis | |
| 2005/0033353 A1 | 2/2005 | Jones | |
| 2005/0165429 A1 * | 7/2005 | Douglas et al. | 606/157 |

* cited by examiner

VESSEL OCCLUSION CLIP AND APPLICATION THEREOF

BACKGROUND

1. Field of the Art

The present embodiments relate to devices and methods or occluding bodily vessels. More particularly, the embodiments relate to methods and devices for a vas-occlusive procedure, including a spring clip that permanently occludes the vas deferens.

2. Description of Related Art

The vasectomy is one of the most common male sterilization techniques, providing an effective long-term contraception method. Typically, in a vasectomy procedure the vas deferens, the vessel connecting the testicles to the prostate, is cut with the cut ends cauterized or sealed shut with suture or clips, typically with a portion of the vas being removed. While this procedure is highly effective for contraception, its results are permanent. The reversal of a vasectomy performed in this way is difficult requiring a microsurgical procedure to re-attach the severed ends of the vas deferens. Typically the reversal procedure cannot be performed endoscopically, which increases patient discomfort and recovery time. Moreover, the success rates of the reversal procedure are not very high—some patients never regain full functionality.

Other non-surgical methods and devices have been developed, such as the insertion of an intra-vas device that blocks or plugs the vas. For example, a device having a plug and a collar may be applied to a vessel such that when the plug is inserted into the lumen of the vas to block the vessel, a collar surrounds the vas to prevent it from dilating.

Another non-surgical method involves the occlusion of the vas deferens with a locking clip or clamp, whereby locking the clip or clamp effectively seals the vessel, blocking flow therethrough. The locking clip may be inserted and locked endoscopically.

The description herein of certain advantages of known devices and methods is not intended to limit the scope of the embodiments. Indeed, the embodiments may include some or all of devices and methods described above without suffering from the same disadvantages.

SUMMARY

It is a feature of an embodiment to provide a vessel occlusion clip having a spring coil, a first leg, and a second leg. The spring coil has a first terminal end and a second terminal end. The first leg is joined on its proximal end with the first terminal end of the spring coil. The second leg is joined on its proximal end with the second terminal end of the spring coil. Each of the first and second legs comprises a vessel occlusion portion comprising an inner surface adapted to contact and occlude a vessel. The inner surface of each vessel occlusion portion has a proximal projection extending inward from the proximal end of the vessel occlusion portion, a distal projection extending inward from the distal end of the vessel occlusion portion, and a substantially planar central region disposed therebetween. The spring coil provides a torsional force that biases the first and second legs inward toward a closed position, in which at least a portion of the distal projections of the vessel occlusion portions of said first and second legs are in forced contact, and at least a portion of the proximal projections of the vessel occlusion portions of said first and second legs are in forced contact, forming a vessel occluding space between the substantially planar central regions of the vessel occlusion portions of said first and second legs.

It is another feature of an embodiment to provide an applicator for implanting an occlusion clip. The applicator has an applicator having a front end and a back end and a tapered applicator tip at the front end, having an opening therein. The applicator has a clip guide at least partially located within the applicator tip, and extending through the opening. The clip guide has a pivotally connected upper and lower guide jaws configured to pivot between an open and a closed position. The guide jaws each comprise a least one longitudinally extending groove adapted to slidingly engage a occlusion clip. The applicator also has a first pusher arm disposed within the housing that is adapted to move the clip guide jaws from the open position to the closed position by pushing on at least one of the upper guide jaw and the lower guide jaw. The applicator has a second pusher arm disposed within the housing, that is adapted to slide an occlusion clip forward in the longitudinally extending grooves of the clip guide. The applicator has an actuator that is adapted to be manipulated from the exterior of the applicator housing and moves between an initial position and a triggered position. The actuator is operably coupled with the first pusher arm and the second pusher arm. Manipulation of the actuator to the triggered position causes the first pusher arm to move the guide jaws from the open position to the closed position, and causes the second pusher arm to slide the occlusion clip forward along the longitudinally extending grooves until the clip is expelled from the clip guide.

It is yet another feature of an embodiment to provide a method for occluding a target vessel. The method involves providing an occlusion clip comprising a first leg, a second leg, and a spring coil joined to the proximal end of the first leg and the second leg. The first and second legs each has at its distal end a pair or laterally-extending clip guide projections. The method further includes providing a clip applicator for manipulating and implanting an occlusion clip about the target vessel. The clip applicator comprises a housing having an applicator tip and a clip guide located adjacent the applicator tip for receiving, manipulating and ejecting the occlusion clip. The clip guide has upper and lower jaws each configured for receiving a portion of the occlusion clip and for slidably engaging and guiding the at least one clip guide projection of either the first or second leg. The upper and lower jaws are pivotably connected for rotation between an open jaw position and a closed jaw position. The method further includes pre-loading the occlusion clip into the clip applicator so that each pair of laterally-extending clip guide projections is engaged by and seated within a corresponding one of said guide jaws and so that the spring and the proximal ends of the legs are oriented in a proximal direction relative to the clip applicator. With the upper and lower jaw guides in the open jaw position, the method comprises manipulating the clip applicator so that the upper and lower guide jaws of the clip guide surround a target vessel. The method also comprises causing the upper and lower jaws to move from the open jaw position to the closed jaw position to engage the target vessel and causing the occlusion clip to slide in a distal direction along the upper and lower jaws until the laterally extending clip guide projections drop out of the respective grooves of the upper and lower guide jaws. This allows the clip to close about the target vessel.

These and other objects, features, and advantages of the present invention will appear more fully from the following description of the exemplary embodiments of the invention.

BRIEF DESCRIPTION OF THE DRAWINGS

The present invention, together with further objects and advantages, may best be understood by reference to the following description taken in conjunction with the accompanying drawings, in the several Figures of which like reference numerals identify like elements, and in which.

These and other objects, features and advantages will appear more fully from the following detailed description of the preferred embodiments.

DETAILED DESCRIPTION OF PREFERRED EMBODIMENTS

Various embodiments described herein provide devices and methods for temporarily or permanently occluding bodily vessels, such as the vas deferens. For purposes of clarity and illustration only, the present embodiments generally are described in relation to vasectomy clips and clip application devices. It should be appreciated, however, that the devices and methods described herein are not limited to these specific embodiments and details, which are exemplary only. It is further understood that one possessing ordinary skill in the art, in like devices and methods, would appreciate the use of the invention for its intended purposes and benefits in any number of alternative embodiments, depending on specific design and other needs.

The embodiments will now be described more fully with reference to the accompanying drawings in which some, but not all, embodiments are illustrated.

Figure 1:
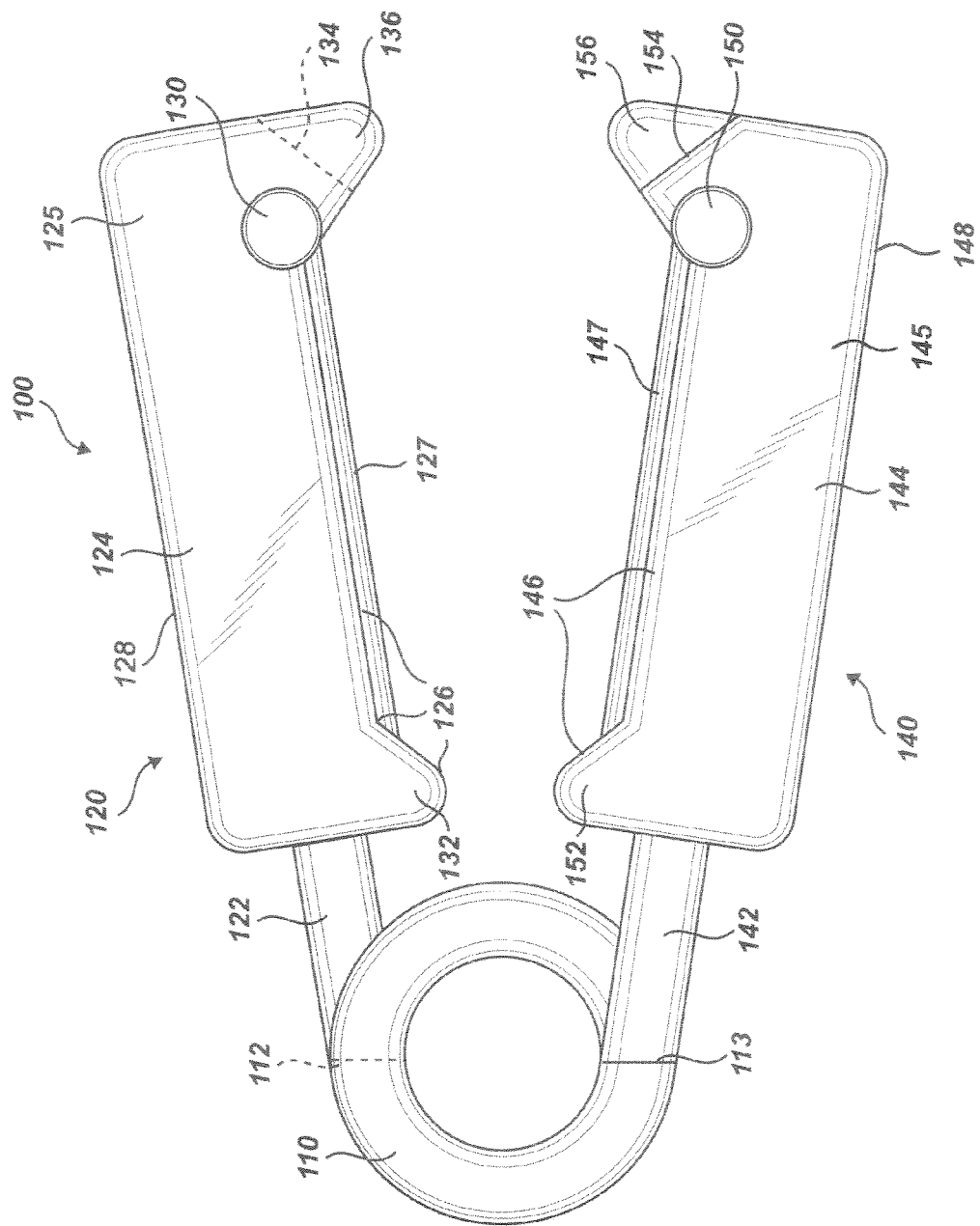
FIG. 1 is an elevational view of a clip in its opened position, according to at least one embodiment.
Figure 2:
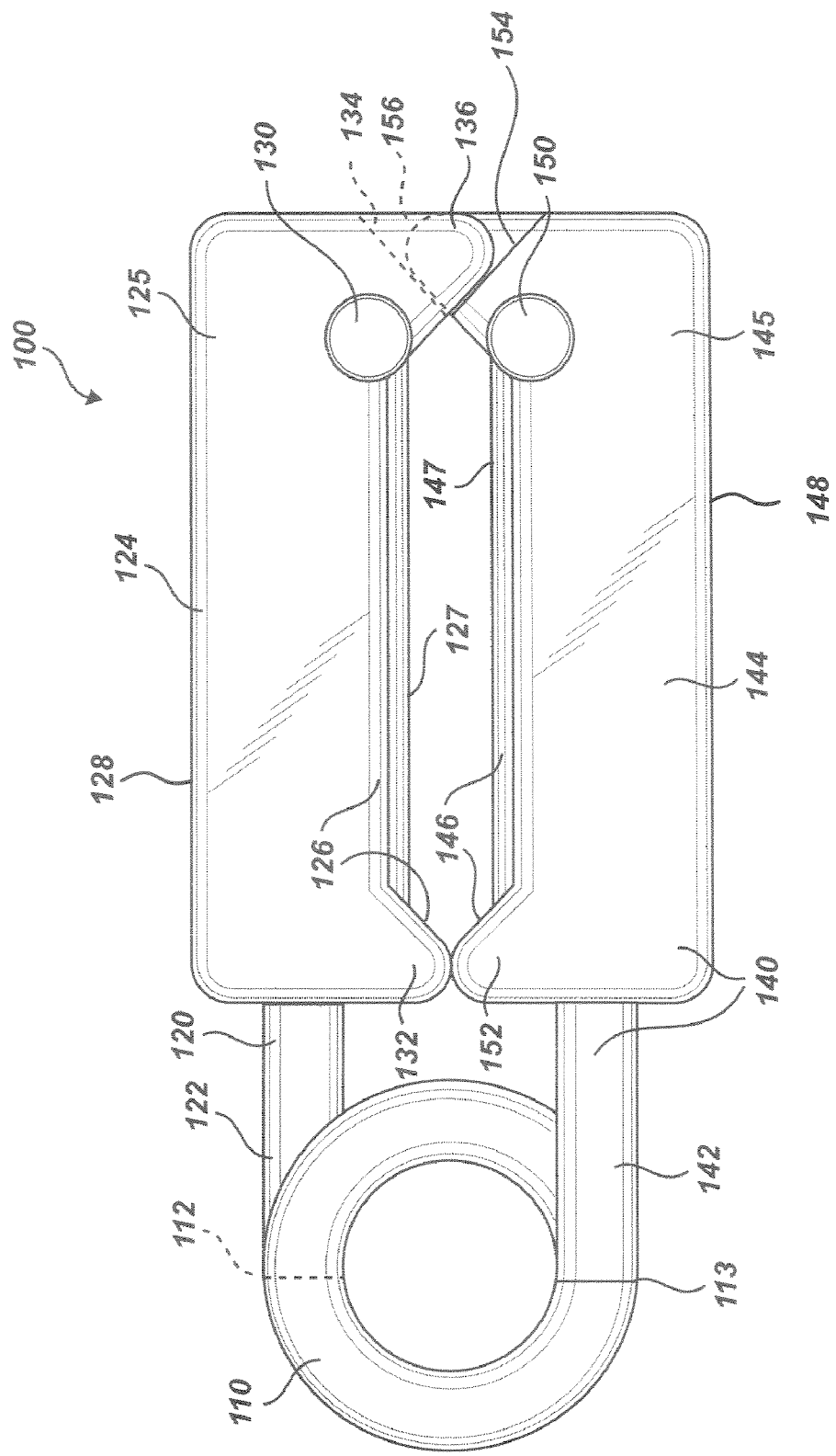
FIG. 2 is an elevational view of a clip in its closed position, according to at least one embodiment.
Figure 3:
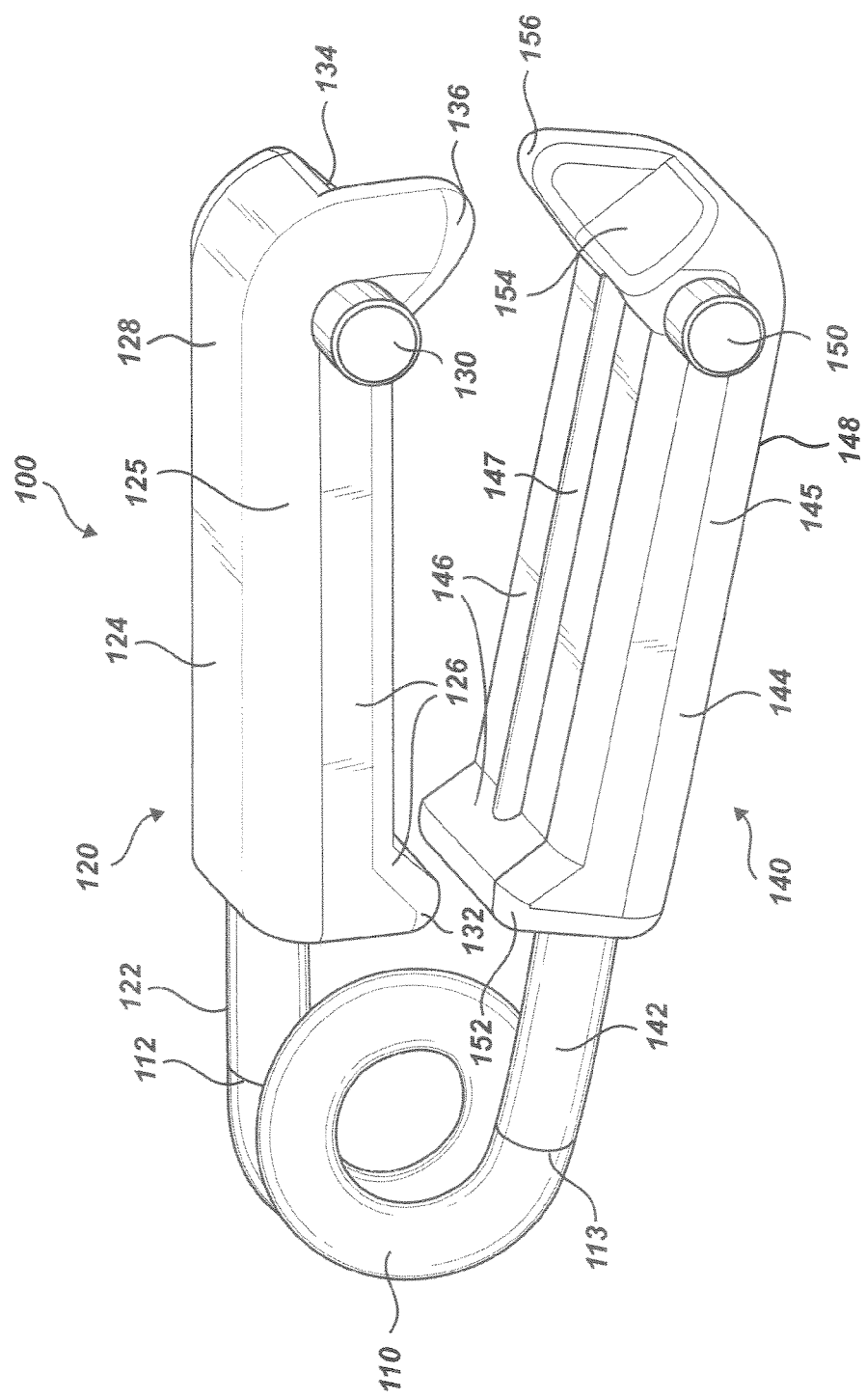
FIG. 3 is a perspective view of a clip in its opened position, according to at least one embodiment.
Figure 4:
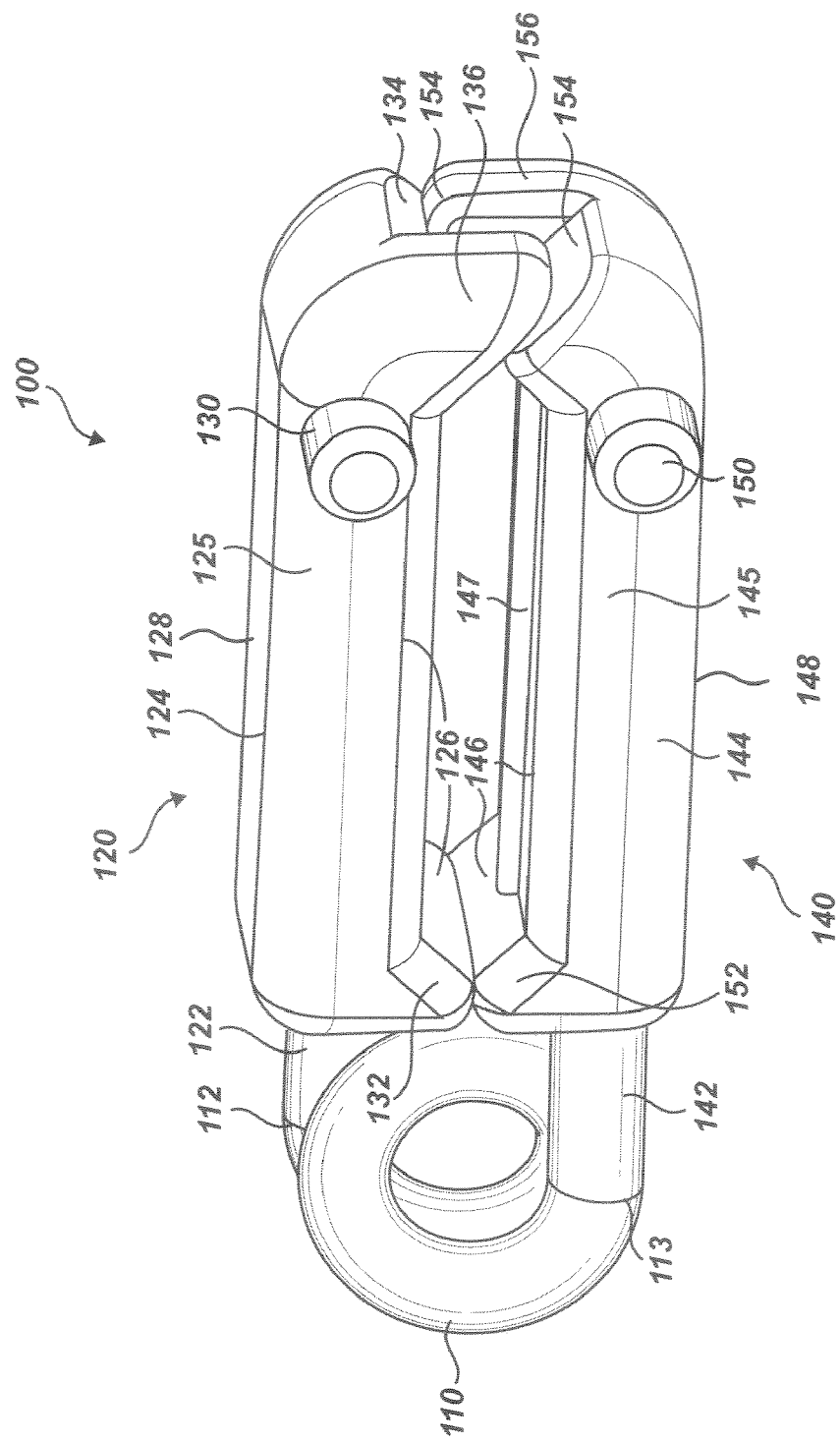
FIG. 4 is a perspective view of a clip in its closed position, according to at least one embodiment.

With reference to FIGS. 1-5, a vas-occlusive clip 100 according to an embodiment will be discussed in more detail. The clip 100 of this embodiment generally has a spring coil 110 attached to a first leg 120 and a second leg 140. The first leg 120 and second leg 140 generally extend in a longitudinal direction with respect to the clip 100. First leg 120 has a spring connector portion 122 proximal to and joined to spring 110 at first spring end 112. On the distal portion of first leg 120 is a vessel occlusion portion 124. Similarly, second leg 140 has a spring connector portion 142 proximal to and joined to spring 110 at second spring end 114, and a distal vessel occlusion portion 144. The clip is configured so that spring 110 maintains a positive force between first and second legs, keeping the clip substantially permanently in its closed position, as shown in FIGS. 2 and 3. To open the clip 100, as shown in FIG. 1, a separating force must be applied to overcome this spring force and separate legs 120 and 140. As discussed in more detail below, an applicator device may be used to open the clip and apply it to a vessel.

Figure 5:
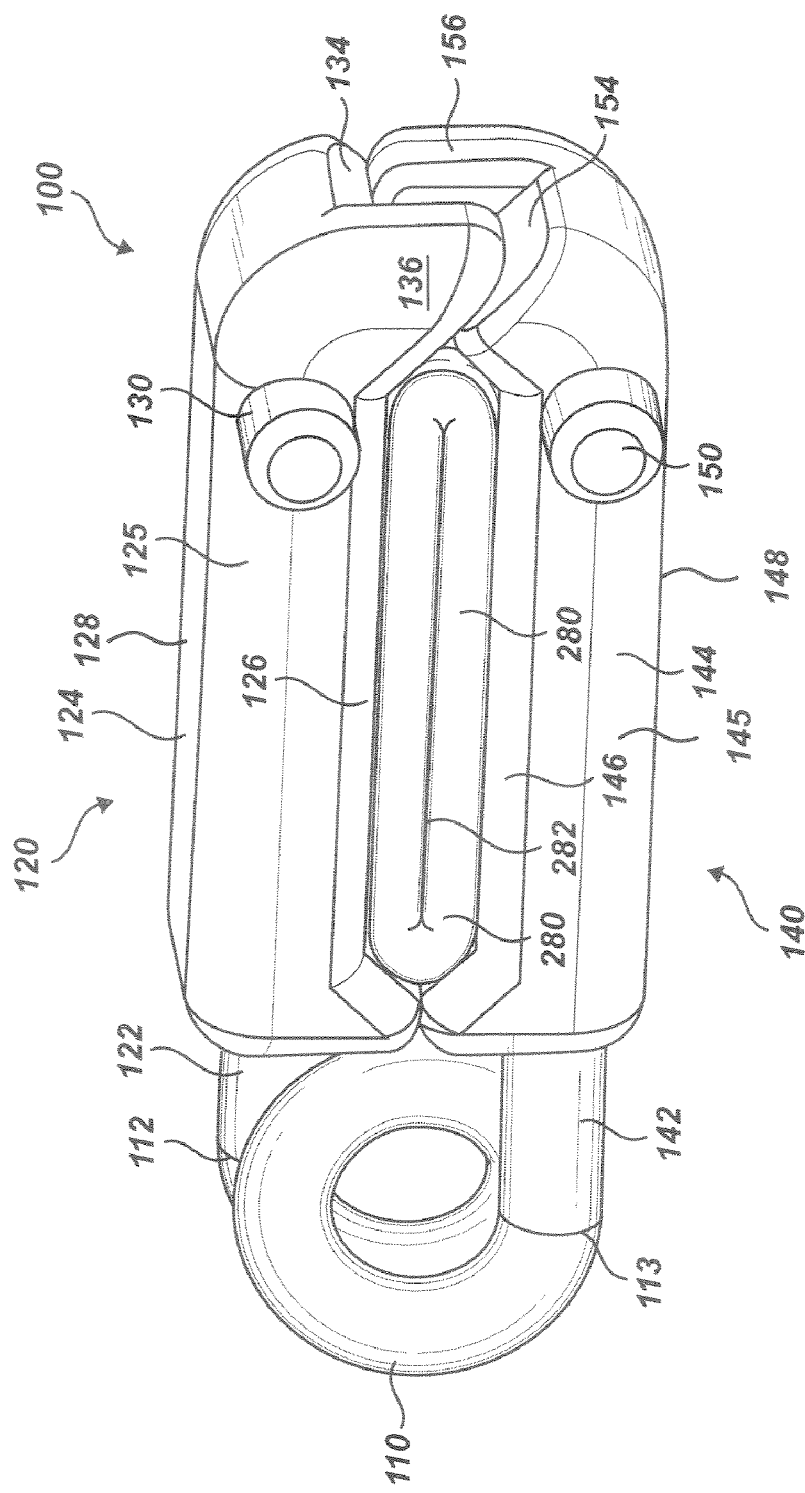
FIG. 5 is a perspective view of a clip in its closed position, with an occluded vessel within the clip, according to at least one embodiment.

As shown in FIG. 5, when clip 100 is applied to a vessel, and is closed, the vessel occlusion portions 124, 144 close around the vessel wall 280, causing an occlusion of the vessel. Where the clip is applied to the vas deferens, the occlusion of the vessel provides effective sterilization by preventing the passage of sperm through the occluded portion of the vas.

The clip preferably is designed to provide a compressive but non-scissoring action to the occluded vessel. As shown in the Figures, spring ends 112 and 114 extend from opposite sides of the spring coil, so that the distance in the transverse direction between spring ends 112 and 114 is roughly equivalent to the width of the spring coil. Consequently, spring connector portions 122 and 142, which are joined to and extend from the spring ends, are laterally spaced at a distance roughly equivalent to the width of the spring coil, each being laterally spaced from the longitudinal centerline of the clip. Spring connector portions 122 and 124 also are vertically spaced at a distance roughly equivalent to the height of the spring coil.

Each spring connector portion 122 and 142 is joined on its distal end to a respective vessel occlusion portions 124 or 144. Vessel occlusion portion 124 is defined in part by an inner tissue contact surface 126 and an outer surface 128, which are connected by side surfaces 125. Likewise, vessel occlusion portion 144 is defined in part by an inner tissue contact surface 146 and an outer surface 148, connected by side surfaces 145. Each of inner tissue contact surfaces 126 and 146 generally is defined by a generally planar central surface (127, 147), an inward extending projection near the proximal end (132, 152) and inward extending projection near the distal end (136, 156). As illustrated in the Figures, the inward extending projections 132, 152, 136, 156 have a tapered configuration but it is understood that projections 132, 152, 136, 156 may have any shape suitable for the exemplary embodiments described herein. Preferably, the surfaces, edges, and corners of vessel occlusion portions 124 and 144 have radiused contours so as not to provide a sharp edge that may sever the occluded vessel, or other tissue.

When the clip 100 is in its closed position, opposed inner tissue contact surfaces 126 and 146 are brought together in an opposed facing relationship, wherein at least a portion of opposed inner tissue contact surfaces 126 and 146 forcibly abut. Preferably, when the clip is in the closed position, the inner tissue contact surfaces 126 and 146 have substantially the same transverse and longitudinal dimensions, and their respective transverse and longitudinal axes are aligned. With the inner tissue contact surfaces 126, 146 in an aligned configuration, the closed clip exerts a compressive rather than shearing or scissoring force on the occluded vessel.

To prevent the first or second leg from shifting in a transverse direction under the torsional closure force provided by the spring, a transverse alignment mechanism may be provided. For example, one or more transverse alignment elements may be provided on the distal edges of vessel occlusion portions 124 or 144, to ensure that opposed vessel occlusion portions of the first leg 120 and second leg 140 remain aligned when the clip is in a closed position. As shown in the embodiment illustrated in FIGS. 1-5, the distal edge of vessel occlusion portion 124 has a transverse alignment element 136, and the distal edge of vessel occlusion portion 144 has a transverse alignment element 156. The transverse alignment elements provide a transverse mechanical interference point on the vessel occlusion portions, preventing the first leg 120 and second leg 140 from skewing transversely under the force of the spring, or under external forces. As illustrated in FIGS. 1-3, the transverse alignment elements 136,156 also beneficially have a dentate shape, which helps to trap the target vessel within the vessel occlusion space as the clip 100 is being closed about it. Persons of ordinary skill in the art, guided by the teachings herein, would appreciate that transverse alignment elements could have alternative shapes, designs, and interference relationships, and would be able to specify the design and configuration of such elements so that they are capable of performing the same or similar functions.

The longitudinal dimension of the inner tissue contact surfaces must be at least large enough that the entire width of the occluded vessel fits between the proximal and distal edges. The overall shape and area of the inner tissue contact surfaces should be designed to optimize the size and stability of the clip and the pressure it exerts on the vessel. One of ordinary skill in the art, guided by the teachings herein, would be able to specify dimensions for the inner surface contact areas so that the clip is suitable for its intended purpose. For example by increasing the area of the inner tissue contact surfaces increases, the pressure exerted by the clip at any given point decreases.

When clip 100 is brought to its closed position, a portion of opposed inner tissue contact surfaces 126, 146 forcibly abut. Preferably, at least a portion of the respective proximal edges (132, 152) and distal edges (134, 154) of opposed inner tissue contact surfaces (126, 146) forcibly abut, leaving a void between the convex central portions of opposed inner tissue contact surfaces. The void between the opposed inner tissue contact surfaces defines a vessel occlusion space, as shown in FIG. 5, when clip 100 is in a closed position about a vessel passes through the vessel occlusion space, and the inner tissue contact surfaces compress the vessel wall therebetween. The vertical dimension of the vessel occlusion space (i.e., the distance between opposed inner tissue contacting surfaces) must be small enough that that the clip can fully occlude a vessel, but not so small that the clip damages the vessel. One of ordinary skill in the art would understand how to design the clip to optimize the vessel occlusion space for this purpose.

Preferably, at least of the inner tissue contacting surfaces has at least one longitudinally extending ridge. In the embodiment shown in FIGS. 1 and 2, the inner tissue contacting surface 126 of vessel occlusion portion 124 has one centrally-located, longitudinally extending ridge 127. Likewise surface 146 has one centrally-located, longitudinally extending ridge 147. The ridge effectively reduces the vessel occlusion space between the inner tissue contacting surfaces, to provide a localized region of greater vessel restriction. This ridge also helps to anchor the clip to the vessel to prevent it from slipping or migrating to a different region. However, when the clip is in a closed position, the ridge or ridges do not come in direct contact with the opposed inner tissue contacting surface. Preferably the one or more ridges are rounded so that they do not provide a sharp edge that may sever the occluded vessel or other tissue. When clip 100 is a closed position, ridges 127 and 147 generally are vertically aligned with each other, to create a region of greater restriction.

The spring 110 provides a biased torsional force to legs 120 and 140, forcing them to a closed position. Spring 110 should provide sufficient force to close the clip 100 and occlude the vessel contained therein. One of ordinary skill in the art would appreciate that if spring 110 provides insufficient closure force, then the clip 100 cannot fully occlude the target vessel, which renders the clip ineffective for sterilization purposes.

The force that spring 100 provides to clip 100 is critical to the functionality of the clip. Preferably spring 110 provides from about 0.5 pounds force to about 1.0 pounds force between legs 120 and 140. In addition to closure force, the spring 110 should have sufficient resistance and durability that it will not allow clip 100 to open under normal in vivo conditions. Once implanted, clip 100 is intended to permanently occlude the target vessel throughout the life of the clip 110. If the tissue of the vessel wall changes due to necrosis and peristalsis and the like, spring 110 and clip 100 should continue to maintain occlusion of the vessel. Spring 110 also should be sufficiently flexible to enable the clip 100 to be opened with minimal spring stress so that it may be applied to the vessel with force.

One of ordinary skill in the art, guided by the teachings provided herein, would understand how to design or specify a spring coil suitable for the clip, having the physical properties described herein. For example, one or more of the following parameters may affect the strength and durability of the spring material of the spring coil; number of coil wraps within the spring coil; thickness (gauge) of the coil material; relative angle of the terminal ends of the spring coil. The spring may be constructed of any material suitable for human implantation and capable of providing the other properties mentioned herein. Suitable materials include metals, polymers, ceramics, and the like, or combinations or composites thereof. Preferably, the spring is made of a metal such as tantalum, titanium, stainless steel, or an alloy thereof. More preferably the spring is made of titanium.

Preferably, the configuration of the spring coil of the clips has an advantage of eliminating the need for a latch or hinge while assuring that the torsional closure force does not decrease as the vessel shrinks after application. Preferably, the clip 100 is configured so that when legs 120, 140 are separated, the diameter of the spring coil 110 increases, which decreases the biasing torsional closure force of the spring 110. Conversely, when legs 120, 140 are released so as to return to the closed position, the diameter of the spring 110 decreases, and the biased torsional closure force exerted by spring 110 increases. Thus, the closure force exerted by legs 120 and 140 on a vessel occluded between the legs increases as the legs 120 and 140 approach each other. Where a vessel is occluded by legs 120 and 140, and the vessel becomes smaller because of a reduction in swelling, necrosis, or peristalsis the pressure exerted by the clip 100 on the vessel increases or nominally decreases, maintaining full occlusion on the vessel.

Spring connecting portions 122, 142, should provide sufficient strength, stiffness and resistance to maintain the clip 100 in a closed position for the life of the clip. The spring connecting portions may be made of any material suitable for human implantation and capable of providing the other properties mentioned herein. Suitable materials include metals, polymers, ceramics, and the like, or combinations or composites thereof. The spring connecting portions may be made of the same or different material than the spring. Preferably, the spring connecting portions are made of a metal such as tantalum, titanium, stainless steel, or an alloy thereof. More preferably the spring connecting portions are made of titanium.

Spring connecting portions 122, 142 may be joined to the respective spring ends 112, 114 in any suitable fashion. For example, the spring connecting portion and spring may be joined together by chemical bonding or welding. Alternatively, spring connecting portions and spring may be formed as a single part, with the spring connecting portions extending from the spring coil.

Vessel occlusion portions 124 and 144 may be constructed of any material suitable for human implantation and capable of providing the other properties provided herein. Suitable materials include metals, polymers, ceramics, and the like, or combinations or composites thereof. Preferably, the vessel occlusion portions are constructed of an implantable grade plastic. Vessel occlusion portions 124, 144, may be joined to the respective spring connecting portions 122, 142, in any suitable fashion. Alternatively, the vessel occlusion portion and the spring connecting portion may be constructed as a single part. In one embodiment, vessel occlusion portions 124, 144, are constructed of an implantable grade plastic that is overmolded to the spring connecting portions.

While the purpose of clip 100 is to be implanted into a body, and to occlude a target vessel, such as the vas deferens, various embodiments provide a clip applicator to enable a user (such as a surgeon) to implant the clip, and to attach it about a target vessel to occlude the vessel. As described above, clip 100 is configured so that its initial state it is in the closed position with spring 110 producing a positive closure force against first leg 120 and second leg 140. Therefore, the clip applicator must be configured to overcome the spring force of clip 100, to open the clip to create sufficient space between legs 120 and to receive the target vessel. Preferably, the clip applicator also provides a useful tool for enabling the user to guide the clip 100 to a position in which it can surround the target vessel. Preferably, the applicator provides a mechanism for releasing the clip 100 so that it successfully closes about the target vessel to occlude it.

Figure 6:
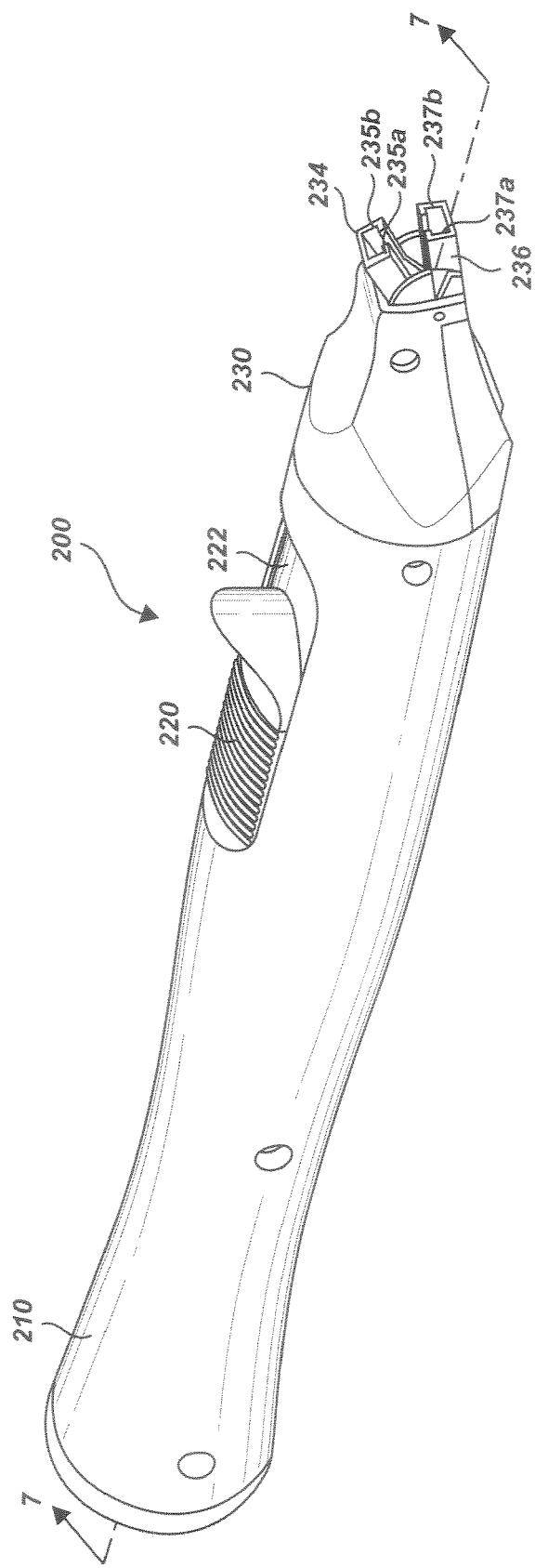
FIG. 6 is a perspective view of a clip applicator, according to at least one embodiment.
Figure 7:
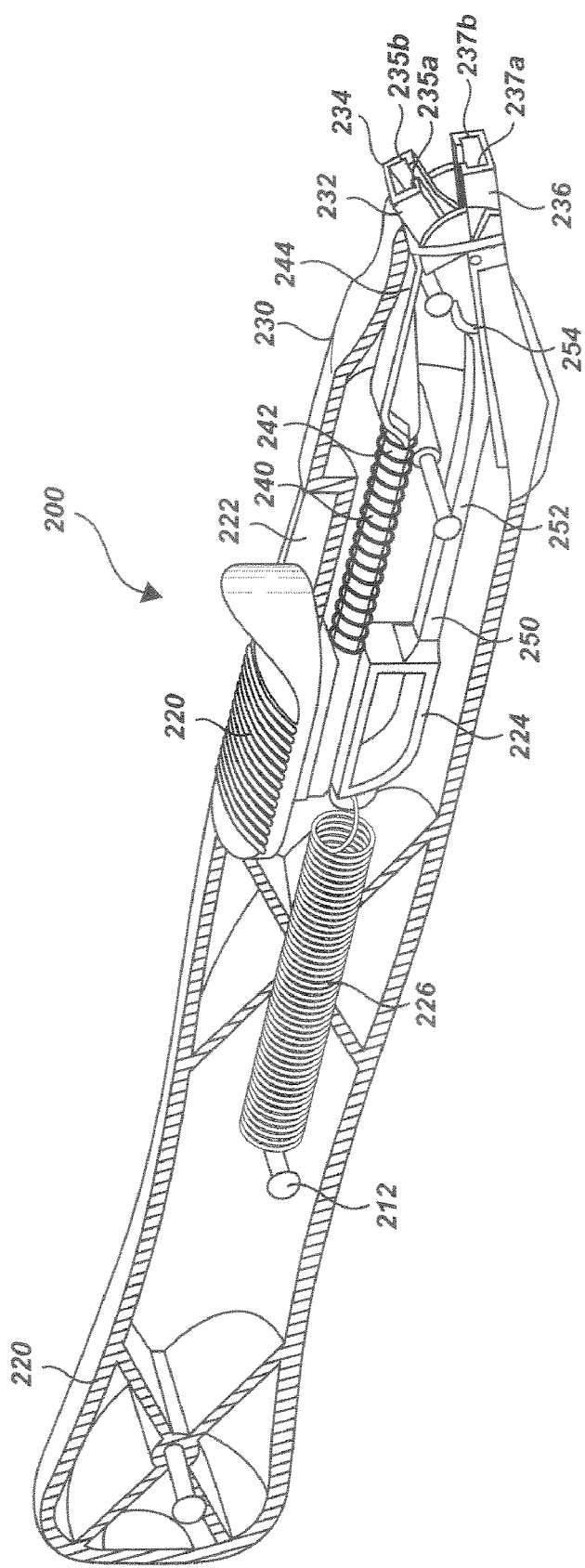
FIG. 7 is a partial sectional view of a clip applicator, shown in perspective, according to at least one embodiment.
Figure 8:
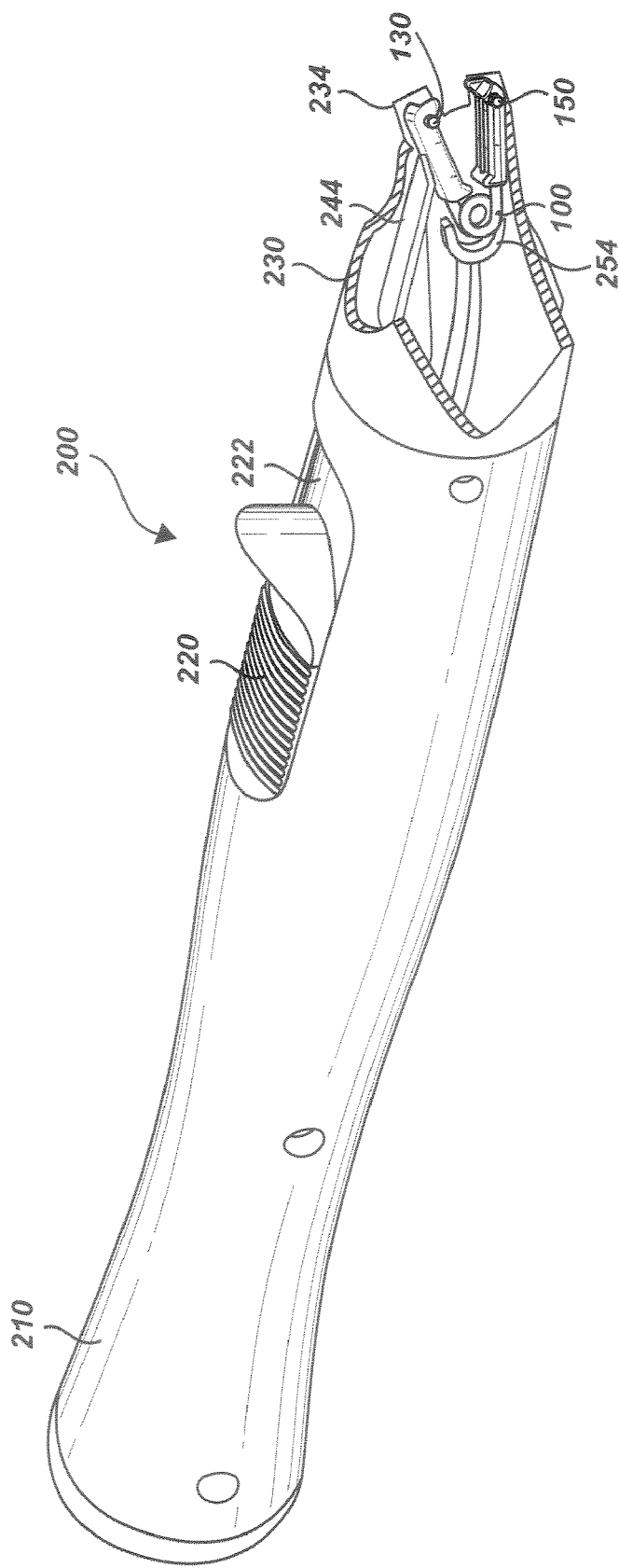
FIG. 8 is a partial sectional view of a clip applicator holding a clip, shown in perspective, according to at least one embodiment.

With reference to FIGS. 6-8, a clip applicator 100 according to an exemplary embodiment will be described. As illustrated in FIG. 6, clip applicator 200 has a housing 210. Housing 210 encloses the internal mechanical parts of the applicator 200, and provides a means for gripping and manipulating the applicator 200. Preferably, housing 210 has a size and shape so that it may be easily manipulated with one hand. Preferably, housing 210 has a longitudinal shaft that is of a suitable size and shape that it may be gripped by a human hand. Housing 210 may be made of a single unitary part capable of performing these functions, or may be provided by the combination of two or more parts that are joined together to perform these functions. Housing 210 may additionally contain certain design elements to improve the ease of use such as, for example, hand contours, finger contours rubber gripping regions, cushioned gripping regions, and the like.

An actuator illustrated in the Figures as slide button 220) is provided on the external surface of the housing 210. The actuator may be manipulated by the user to perform one or more designated functions. An suitable actuator device may be used for this purpose, including mechanical or electrical actuators such as push buttons, slide buttons, triggers, and other like devices. One of ordinary skill in the art, guided by the teachings herein, would understand how to specify an actuator suitable for this device. In certain embodiments, more than one actuator may be provided, each actuator performing designated functions. In FIG. 6, applicator 200 has a single slide button actuator 220 which the user manipulates with a finger or thumb. The slide button 220 is configured to slide forward and backward in the longitudinal direction of the applicator in slide button groove 222. In its initial retracted position (as illustrated in FIG. 6), slide button 222 rests against the back portion of the groove. Preferably, the slide button 220 is anchored in this retracted position, such as with a spring mechanism, so that it will not slide forward without user manipulation. A user must use his or her finger or thumb to push the slide button 220 forward. As slide button 220 moves forward in groove 222, the applicator performs certain functions, described in more detail below.

At one end of the applicator 200 is an applicator tip 230, having an opening 232, from which clip 100 is manipulated and ejected. Preferably, the housing 210 tapers around the applicator tip 230 toward opening 232 so that the tip and opening have a smaller diameter than the rest of the applicator. Preferably, the size or diameter of the tip 230 and opening 232 are small enough to provide good visibility to the user, so that they can see the tip 230 and clip 100, and can guide it into place. Projecting from opening 232 are two leg guides 234 and 236. The leg guides are intended to open and close the legs 120, 140 of clip 100 so that it may be properly implanted. The first leg guide 234 is configured to hold and guide the first leg 120 of clip 100. The second leg guide 236 is configured to hold and guide the second leg 140 of clip 100. First and second leg guides 234 and 236 are pivotally connected so that they open and close in a jaw-like fashion. The proximal edges of guides 234 and 236 re attached to pivot 238, while distal edges of guides 234 and 236 move about the pivot 238 axis. In the embodiment illustrated in FIGS. 6-8, only first leg guide 234 is movably connected to the pivot 238, while second leg guide 236 remains in a fixed position. However, one of ordinary skill in the art would appreciate that one or both of the leg guides could be movably connected to the pivot, without sacrificing functionality of the applicator 200. Preferably, the leg guides and pivot 238 have a biasing mechanism that biases the leg guides 234 and 236 into an opened position until a closing force is applied to them.

As discussed above, and illustrated in FIGS. 1-5, clip 100 has side projections 130 that project from both sides 125 of leg 120, and side projections 150, that project from both sides 145 of leg 140. While the illustrations show one side of the clip 100, it will be understood that the opposite side of clip 100 is substantially similar to that shown. The leg guides 234 and 236 have corresponding grooves 235a and 236b, and 237a and 237b, located along the sides of their interior surfaces. When the clip is properly inserted in the leg guides 234 and 236, side projections 130 are seated in first grooves 233a and 235b, and side projections 150 are seated in second grooves 237a and 237b. When properly seated, the spring end of the clip 100 is directed inwardly, and the vessel occlusion portion of the legs 120, 140 is directed toward the end of the applicator tip 230, as best shown in FIG. 8.

The grooves 235a, 235b and 237a, 237b extend at least a portion of the length of respective leg guides 234 and 236. Each groove is defined on the inner surface of the leg guide by a lip or rail which helps to keep the side projections seated within the leg guide during applicator operation. The grooves provide a means for seating and securing the clip 100 within the applicator tip 230 during use of the applicator 200, and also provide a means for manipulating legs 120, 140 of the clip in the longitudinal and vertical direction so that the clip may be opened, closed, and ejected. For example, side projections may ride forward and back in the longitudinal direction of the groove to enable the clip to be seated and ejected; legs 120 and 140 may be opened or closed when the leg guides 234 and 236 are opened or closed and the grooves exert an opening or closing force against the side projections.

FIG. 7 shows applicator 200 in partial section view, with a portion of the housing removed to show the internal mechanisms of the applicator. As shown in this view, slide button 220 is functionally connected to slide button carriage 224, which is located within the housing 210. In the embodiment of FIG. 5, the slide button 220 and slide button carriage 224 are fixedly connected so that the position of the slide button carriage 224 relative to the slide button 220 does not change during operation of the applicator 200. When the slide button 220 is moves along the slide button groove 222, the slide button carriage 224 moves in the same direction, within the housing 210. In other embodiments, the actuator may be connected by other means to the internal mechanisms of the applicator, such as with suitable mechanical or electrical connection means. One of ordinary skill in the art, guided by the teachings provided herein, would be able to specify various means for connecting the actuator to the internal mechanisms to provide a functional applicator.

Anchor spring 226 is attached on a first end to the slide button carriage 224 and on a second end, to an anchor post 212 that is connected to the housing 210. The anchor spring 226 is a biased spring that exerts a retractive force on the slide button carriage 224, to keep the slide button 220 in a retracted position in the slide button groove 222 when no other forces are applied to the slide button 220. When a user pushes on the slide button 220 with enough force to overcome the retractive force of the anchor spring 226, the slide button 220 moves forward in groove 222, and slide button carriage 224 moves forward in the housing.

The slide button carriage 224 is operably connected to other mechanisms in the housing, to perform certain functions when the slide button 220 moves forward or backward. In the embodiment of FIG. 7, slide button carriage 224 is connected to first pusher arm mechanism 240, and second pusher arm mechanism 250.

First pusher arm mechanism 240 performs the function of forcing first leg guide 234 about its pivot from an opened position (shown in FIG. 6) to a closed position. The pusher arm mechanism 240 has an arm 242 that extends forward in the longitudinal direction of the applicator 200, and is connected at a first end to slide button carriage 224, and at a second end to pusher plate 244. As the slide button carriage 224 moves forward in the applicator 200, it moves pusher arm 242 and plate 244 forward with it. Pusher plate 244 translates the forward force of the arm 242 to a tangential force against the outer surface of first leg guide 234. In its initial, open position, first leg guide 234 is positioned at an angle to the longitudinal axis of the applicator 200. As plate 244 moves forward, it glides against the top or outer surface of first leg guide 234, pushing the guide about pivot 238 toward second leg guide 236. When the plate 244 is in its forward-most position, leg guide 234 is in its fully closed position. As explained in more detail above, the movement of the leg guide 234 to a closed position also causes the clip 100 that is seated in the leg guides to move toward its closed position.

Second pusher arm mechanism 250 performs the function of pushing the clip 100 longitudinally within the applicator 200, and eventually ejecting clip 100 from the tip of the applicator 200. Second pusher arm mechanism 250 has arm 252 that extends in the longitudinal direction of the applicator 200, and is joined on one end to slider button carriage 244. The opposite end of arm 252 terminates with a cradle 254 that is adapted to push on the spring end of clip 100, and move it in longitudinal direction, corresponding to the action of 252. Ultimately, when slide button carriage 224 is substantially in its fully forward position, the arm 252 and cradle 254 eject the clip 100 from the applicator tip 230. Preferably, the second pusher arm mechanism 250 is configured so that it does not engage clip 100 until after the first pusher arm mechanism 240 has started to close first leg guide 234, and even more preferably the second pusher arm mechanism 250 is configured so that it does not engage clip 100 until after the first pusher arm mechanism has fully closed first leg guide 234. Once the cradle 254 engages the spring end of clip 100, it pushes it in the longitudinal direction. As it is being pushed, the side projections 130 and 150 slide forward within the respective grooves 235a, 235b, 237a and 237b in the leg guides 234 and 236. The proximal end of each of the grooves is open, so that when the side projections are forced beyond the proximal end, they slide out of the grooves, and the clip is released from the guides and ejected from the tip. Once the clip 100 is fully ejected from applicator 200, the spring action of the clip 100 keeps the clip in its fully closed position.

In the embodiment described above, the actuator provides a two-stage action. As slide button 220 (the actuator) moves forward, the first pusher arm mechanism 240 engages the first leg guide 134, closing it about pivot 238, which closes clip 100. Then, as the slide button 220 continues to move forward, the second pusher arm mechanism 250 engages the spring end of clip 100 and pushes it forward in the leg guides, until it is ejected from the applicator.

In other embodiments, the actuator may trigger alternative, or additional functions. For example, certain embodiments provide a means for retracting the leg guides (or other equivalent devices) may retract away, from the clip and occluded vessel during the ejection process. Other embodiments provide additional means for assisting the user in isolating and manipulating the target vessel into the proper location of the clip. One of ordinary skill in the art, guided by the teachings herein, would understand how to use the applicator to perform such alternative or additional functions to improve the capability of the applicator.

The applicator 200, and its various components may be formed from any material suitable for use as described herein. Because the applicator will be used in a medical procedure, the materials should be capable of sterilization. Many of the parts will beneficially be constructed of a moldable material, such as a polymer, so that the various contours and features may be provided in the mold design, rather than separately attached.

The applicator and clip described above are useful in medical procedures requiring permanent occlusion of a vessel. One exemplary procedure is a vasectomy procedure, in which the vas deferens vessels are targeted for occlusion. In an exemplary embodiment, a user such as a surgeon, may occlude a vas deferens vessel using the applicator 200 and clip 100. In this embodiment, one or more applicators 200 may be provided to the user for the procedure. Preferably the one or more applicators 200 are provided to the user in a sterilized condition. Preferably, the one or more applicators are provided to the user with a clip 100 reloaded, such that the side projections 130 and 150 of clip legs 120, 140, are seated in the grooves 235a, 235b, 237a, 237b of respective leg guides 234, 236. The clip 100 may be pre-loaded in an open position, or in a closed position. If the clip 100 is provided in the closed position, then the applicator must have a means, such as an actuator, for opening the clip 100. The opened clip 100 should be configured in the applicator 200 so that the opened end of the clip faces outward, providing a region for receiving the target vessel.

In alternative embodiments, the applicator 200 may be provided to the user without a loaded clip, so that the user must load a clip. In such instances, the user may require training as to how to load the clip. One or more additional clip loading devices may be provided to assist the user in loading the clip into the applicator. However, the consistency may be improved where the clip is preloaded in the applicator 200 for the user. In other embodiments, the applicator 200 may be adapted to be preloaded with multiple clips, such as a cartridge of clips. However, because this applicator is designed to be used in a sterile medical procedure, it is preferred that a single-use applicator be provided to the user with one preloaded clip.

The user may prepare the region for implantation using any suitable means. Once the target vessel is located and is made accessible to the user, then the applicator 200 may be used to implant or attach the clip 100 the target vessel. The user may isolate the target vessel, and manipulate the vessel and the applicator 200, to place the vessel between the legs 120, 140 of open clip 100, so that the vessel lies in a transverse direction across the vessel occlusion portions 122, 142 of the legs, with the entire cross section of the vessel contained within this region. Once the user has managed to manipulate the vessel into this location, the user pushes the slide button actuator 220 forward, activating the first pusher arm mechanism 240, which closes first guide leg 234 about its pivot 238, as described in more detail above. Once the slide button actuator 220 is pushed far enough forward, the first guide leg 234 fully closes, and the clip 100 closes about the vessel, occluding the vessel.

The user will then continue to push the slide button actuator 220 forward, activating the second pusher arm mechanism 250, which pushes the clip 100 in the longitudinal direction toward and out of the applicator tip 230. During this longitudinal movement, the side projections 130 and 150 of clip 100 glide along corresponding grooves 235a, 235b, 237a, 237b in the leg guides 234, 236. Once the slide button actuator 220 is pushed far enough forward, the side projections drop out of their respective grooves, so that the clip 100 is ejected from the applicator 200. At this point, the clip 100 is in a fully closed position, occluding the target vessel.

Once used, the applicator 200 may be disposable, or may be reusable. For example, in an embodiment in which applicator 200 is reusable, applicator 200 may be returned to the manufacturer or distributor so that it may be sterilized, preloaded, and packaged so that it may be reused. Preferably, the applicator 200 is made disposable.

While clip 100 is intended to provide permanent occlusion of a vessel, preferably clip 100 may be removed from the vessel, enabling fluid communication through the vessel. To remove the clip 100, a user must apply an opening force to legs 120, 140, that is sufficient to overcome the closing force provided by spring 110. The user may use a device similar to clip applicator 200 to remove the clip. Preferably a clip removal device is configured to open legs 120, 140, such as by attaching to side projections 130 and 150, and applying a force to the projections to open the legs.

The embodiments of the present inventions are not to be limited in scope by the specific embodiments described herein. Various modifications are intended to fall within the scope of the following appended claims. Further, although some of the embodiments of the present invention have been described herein in the context of a particular implementation in a particular environment for a particular purpose, those of ordinary skill in the art should recognize that its usefulness is not limited thereto and that the embodiments of the present inventions can be beneficially implemented in any number of environments for any number of purposes. Accordingly, the claims set forth below should be construed in view of the full breadth and spirit of the embodiments of the present inventions as disclosed herein. While the foregoing description includes many details and specificities, it is to be understood that these have been included for purposes of explanation only, and are not to be interpreted as limitations of the invention. Many modifications to the embodiments described above can be made without departing from the spirit and scope of the invention.

What is claimed is:

1. A vessel occlusion clip, comprising:
a spring coil having a first terminal end and a second terminal end;
a first leg joined on a proximal end with the first terminal end of the spring coil;
a second leg joined on a proximal end with the second terminal end of the spring coil,
wherein each of the first and second legs has a distal end and comprises a vessel occlusion portion comprising an inner surface adapted to contact and occlude a vessel, said vessel occlusion portion further comprising on its inner surface a proximal projection extending inward from a proximal end of the vessel occlusion portion adjacent the proximal end of each of the first and second legs, a distal projection extending inward from a distal end of said vessel occlusion portion adjacent the distal end, and a planar central region extending from the proximal projection to the distal projection, and
wherein said spring coil provides a torsional force that biases said first leg and said second leg inward toward a closed position in which the distal projections of the vessel occlusion portions of said first and second legs are in forced contact with one another, the proximal projections of the vessel occlusion portions of said first and second legs are in forced contact with one another, and said planar central region of said first leg opposes and is spaced apart from said planar central region of said second leg by a spacing distance determined at least in part by a dimension of each of the proximal projections, thereby forming a vessel occluding space between the planar central regions of the vessel occlusion portions of said first and second legs; and
a transverse alignment mechanism to keep the first and second legs aligned in the closed position, said transverse alignment mechanism comprising:
a first alignment projection extending inward from the distal end of the vessel occlusion portion of the first leg, and
a second alignment projection extending inward from the distal end of the vessel occlusion portion of the second leg,
wherein said first alignment projection provides a mechanical interference point to prevent the second leg from shifting in a transverse direction under the torsional force provided by the spring, and
wherein said second alignment projection provides a mechanical interference point to prevent the first leg from shifting in a transverse direction under the torsional force provided by the spring.

2. The clip recited in claim 1, wherein at least one of said proximal projections is a tapered projection.

3. The clip recited in claim 1, wherein at least one of said distal projections is a tapered projection.

4. The clip recited in claim 1, wherein each of said first and second legs further comprises at least one transversely-extending, cylindrical clip-guide projection on its distal end.

5. The clip recited in claim 1, further comprising at least one longitudinally extending ridge projecting from the planar central region of the inner surface of the vessel occluding portion and extending from the proximal projection to the distal projection of at least one of said first and said second legs.

6. The clip recited in claim 1, wherein said spring provides a torsional force of from 0.5 pounds force to 1.0 pounds force.

7. The clip recited in claim 1, wherein:
said first alignment projection has a first laterally facing surface intermediate the distal end of the vessel occlusion portion of the first leg and an inwardly extending first alignment projection tip,
said second alignment projection has a second laterally facing surface intermediate the distal end of the vessel occlusion portion of the second leg and an inwardly extending second alignment projection tip, and said first and second laterally facing surfaces being in lateral opposition when said clip is in said closed position.

8. The clip recited in claim 7, wherein the mechanical interference point of the first alignment projection is part of the first laterally facing surface and the mechanical interference point of the second alignment projection is part of the second laterally facing surface.

9. The clip recited in claim 1 wherein the spring coil comprises a plurality of coil wraps.

10. The clip recited in claim 1 wherein the proximal projection and the distal projection are spaced apart by a distance greater than or equal to a width dimension of the vessel after occlusion.

11. The clip recited in claim 1 wherein the spring coil is formed from metal and the vessel occlusion portion is formed from plastic.

12. A vessel occlusion clip, comprising:
- a spring coil having a first terminal end and a second terminal end;
- a first leg joined on a proximal end with the first terminal end of the spring coil; and
- a second leg joined on a proximal end with the second terminal end of the spring coil;
- wherein each of the first and second legs has a distal end and comprises a vessel occlusion portion comprising an inner surface adapted to contact and occlude a vessel; said vessel occlusion portion further comprising on its inner surface a proximal projection extending inward from a proximal end of the vessel occlusion portion adjacent the proximal end of each of the first and second legs, a distal projection extending inward from a distal end of said vessel occlusion portion adjacent the distal end, a planar central region extending from the proximal projection to the distal projection and having first and second lateral edges, and a longitudinal ridge projecting inward from the planar central region and extending from the proximal projection to the distal projection, the longitudinal ridge being spaced apart from each of the first and second lateral edges;
- wherein said spring coil provides a torsional force that biases said first leg and said second leg inward toward a closed position in which at least a portion of the distal projections of the vessel occlusion portions of said first and second legs are in forced contact with one another, at least a portion of the proximal projections of the vessel occlusion portions of said first and second legs are in forced contact with one another, and said planar central region of said first leg opposes and is spaced apart from said planar central region of said second leg by a spacing distance determined at least in part by a dimension of each of the proximal projections, thereby forming a vessel occluding space between the central regions of the vessel occlusion portions of said first and second legs.

13. The clip recited in claim 12 wherein the longitudinal ridge has a rounded inward facing surface.

* * * * *